United States Patent
Ikeda et al.

(10) Patent No.: US 7,912,269 B2
(45) Date of Patent: Mar. 22, 2011

(54) MEDICAL IMAGE PROCESSING APPARATUS AND METHOD OF PROCESSING MEDICAL IMAGE

(75) Inventors: Yoshihiro Ikeda, Nasushiobara (JP); Miwa Okumura, Nasushiobara (JP); Kohsuke Kudo, Sapporo (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1708 days.

(21) Appl. No.: 11/092,899

(22) Filed: Mar. 30, 2005

(65) Prior Publication Data
US 2006/0004279 A1    Jan. 5, 2006

(30) Foreign Application Priority Data

Mar. 31, 2004    (JP) ................ P2004-108291

(51) Int. Cl.
   *G06K 9/00*    (2006.01)
   *G06K 9/34*    (2006.01)

(52) U.S. Cl. ............... 382/131; 382/132; 382/173

(58) Field of Classification Search ............ 382/131, 382/132, 173
See application file for complete search history.

(56) References Cited

U.S. PATENT DOCUMENTS

| | | | |
|---|---|---|---|
| 5,148,809 A * | 9/1992 | Biegeleisen-Knight et al. | 600/443 |
| 6,718,055 B1 * | 4/2004 | Suri | 382/128 |
| 7,774,041 B2 * | 8/2010 | Nambu et al. | 600/407 |

FOREIGN PATENT DOCUMENTS

| | | |
|---|---|---|
| JP | 2002-301064 | 10/2002 |
| JP | 2003-116843 | 4/2003 |
| JP | 2003-175022 | 6/2003 |
| JP | 2003-190148 | 7/2003 |
| JP | 2003-225234 | 8/2003 |

OTHER PUBLICATIONS

Kohsuke Kudo, et al., "Quantitative Cerebral Blood Flow Measurement with Dynamic Perfusion CT Using the Vascular-Pixel Elimination Method: Comparison with $H_2^{15}O$ Positron Emission Tomography", AJNR. American Journal of Neuroradiology, XP-002359210, vol. 24, No. 3, Mar. 2003, pp. 419-426.

Thomas Ernst, et al., "Correlation of Regional Cerebral Blood Flow From Perfusion MRI and Spect in Normal Subjects", Magnetic Resonance Imaging, XP-002359211, vol. 17, No. 3, Apr. 1999, pp. 349-354.

Office Action issued Aug. 3, 2010, in Japan Patent Application No. 2005-086672.

* cited by examiner

*Primary Examiner* — Bhavesh M Mehta
*Assistant Examiner* — Utpal Shah
(74) *Attorney, Agent, or Firm* — Oblon, Spivak, McClelland, Maier & Neustadt, L.L.P.

(57) ABSTRACT

According to a medical image processing apparatus, a data of a region of the blood vessel is removed from respectives of a plurality of sheets of original image data collected by scanning a subject injected with a contrast medium by a medical modality, thereafter, a pixel value of the region of the blood vessel is substituted for by pixel values of a plurality of pixels present at a surrounding of the region, the plurality of sheets of original image data including the substituted region of the blood vessel are subjected to a preprocessing including a noise removing processing and a pixel bundling processing, and circulation dynamic state information of perfusion of a substantial portion is analyzed from the plurality of sheets of original image data subjected to the preprocessing.

17 Claims, 8 Drawing Sheets

MEDICAL IMAGE PROCESSING APPARATUS AND METHOD OF PROCESSING MEDICAL IMAGE

BACKGROUND OF THE INVENTION

1. Field of the Invention

The present invention relates to a medical image processing apparatus and a method of processing a medical image for processing image data collected by a medical modality of an X-ray CT scanner or the like, particularly relates to a medical image processing apparatus and a method of processing a medical image accompanied by a step of removing a region of the blood vessel from an image.

2. Description of the Related Art

In a field of medical diagnosis based on an image collected by a medical modality, an X-ray CT scanner constitutes one of central presences thereof.

By using an image provided by the X-ray CT scanner as a simple CT image as it is, morphologic information in a subject can be provided. Further, it is frequently carried out to execute dynamic scanning by imaging CT inspection to provide dynamic information of circulation at a surrounding of a focus as visual information. By appearance of multislicing CT scanner in recent years, high speed scanning can be executed and therefore, it seems that dynamic scanning by imaging CT inspection will further frequently be executed in the future.

As one of the applied example of the dynamic scanning by imaging CT inspection, there is brain blood stream analysis (CT-perfusion) as shown by, for example, JP-A-2003-116843 or JP-A-2003-190148. The dynamic scanning is a method of providing a plurality of sheets of dynamic CT images by repeatedly taking an image of the same region of the head portion of a subject injected with a contrast medium. A time-intensity (CT value) curve (TIC: time intensity curve) representing a time sequential change of the CT values for respective designated regions is obtained by the plurality of sheets of dynamic CT images. According to the brain blood stream analysis, there are calculated parameters of a brain blood flow rate (CBF: Cerebral Blood Flow: a blood flow rate per unit volume and per unit time in the capillary of the brain tissue), a brain blood volume (CBV: Cerebral Blood Volume: a blood volume per unit volume in the brain tissue), a mean transit time (MTT: Mean Transit Time: a mean time period of passing blood through the capillary), a residue (Err: an index of err of shift of a measured value from an analyzing model) from the plurality of sheets of dynamic CT images. The calculated parameters are visualized as, for example, maps to subject to diagnosis.

Since the object portion of the brain blood flow analysis is the brain tissue, it is important not to output a result of measuring the principal blood vessel in the brain and not to reflect the CT value of the blood vessel to a result of measuring the brain tissue. The blood volume of the blood vessel is larger than perfusion of the brain tissue. Therefore, according to the brain blood stream analysis of the related art, generally, a pixel in the blood vessel region is removed by subjecting a result of analyzing the blood volume to a threshold processing (blood vessel removing processing).

However, in the case of the above-described method of removing the blood vessel of the related art, a partial volume of the blood vessel is widened by a filtering processing for removing noise executed in the midst of a processing of analyzing the tissue blood stream and a pixel bundling processing aiming at compression of image data, the pixel value of the blood vessel portion is removed thereafter and therefore, there poses a problem that an effect of the partial volume of the blood vessel remains at an edge portion of a contour contiguous to the removed blood vessel portion. The blood flow rate of the brain tissue is evaluated to be slightly larger by presence of the partial volume effect, which effects an influence on reliability of a result of measuring the blood flow rate.

SUMMARY OF THE INVENTION

Hence, it is an object of the invention to provide a medical image processing apparatus and a method of processing a medical image capable of firmly removing a blood vessel region from an image in a blood stream analysis processing of the above-described brain blood stream analysis or the like in a state in which a partial volume effect thereof hardly remains at a surrounding of the region, thereby, capable of highly accurately and highly reliably executing a measurement with regard to a blood stream analysis by dynamic scanning.

In order to achieve the above-described object, according to an aspect of the invention, there is provided a medical image processing apparatus comprising a blood vessel removing unit configured to remove a data of a region of the blood vessel from a data of an original image collected by scanning a subject injected with a contrast medium by a medical modality, and an analyzing unit configured to analyze circulation dynamic state information of a substantial portion of the subject by applying a preprocessing including a noise removing processing for removing noise to the data of the original image removing the region of the blood vessel by the blood vessel removing unit.

According to other aspect of the invention, there is provided a medical image processing apparatus comprising a blood vessel removing unit configured to remove a data of a region of the blood vessel from respectives of data of a plurality of sheets of original images collected by scanning a subject injected with a contrast medium by a medical modality;

a substituting unit configured to substitute pixel values of a plurality of pixels present at a surrounding of the region for a pixel value of the region of the blood vessel in the respectives of the plurality of sheets of images generated by the blood vessel removing unit, a preprocessing unit configured to execute a preprocessing including a noise removing processing for removing noise of the data for the plurality of sheets of images subjected to a processing by the substituting unit, and an analyzing unit configured to analyze circulation dynamic state information of a substantial portion of the subject from the data of the plurality of sheets of images subjected to the preprocessing by the preprocessing unit.

Further, according to the invention, there is provided an image processing apparatus comprising, curve forming unit configured to form data of time-density curves (TDC) of respectives of data of a plurality of sheets of original images for respective pixels, calculating unit configured to calculate values of areas under curves of the curves of the respective pixels with regard to curve data formed by the time-density curve forming unit, comparing unit configured to compare the values of the areas under curves calculated by the calculating unit with a predetermined threshold, and recognizing unit configured to recognize that portions of the pixels having the values of the areas under the curves exceeding the threshold by the comparing unit fall in the region of the blood vessel.

Further, according to the invention, there is provided an image processing apparatus comprising, a storing apparatus configured to store data of a plurality of sheets of original images collected by scanning a subject injected with a contrast medium by a medical modality, and a processor configured to execute respective processings of removing a data of a region of the blood vessel from respectives of the data of the plurality of sheets of images stored to the storing apparatus, substituting pixel values of a plurality of pixels present at a surrounding of the region for a pixel value of the region of the blood vessel at the respectives of the generated plurality of sheets of images, executing a preprocessing including a noise removing processing for removing noise for the plurality of sheets of image data subjected to the above-described processings, and analyzing circulation dynamic state information of a substantial portion of the plurality of sheets of image data subjected to the preprocessing.

Further, according to the invention, there is provided a medical image processing apparatus comprising, blood vessel removing unit configured to remove a data of a region of the blood vessel from a data of an original image collected by scanning a subject injected with a contrast medium by a medical modality, and analyzing unit configured to analyze circulation dynamic state information of a substantial portion of the subject by applying a preprocessing including a noise removing processing for removing noise to the data of the original image removing the region of the blood vessel by the blood vessel removing unit.

Further, according to the invention, there is provided a medical image processing apparatus comprising, blood vessel removing unit configured to remove a data of a region of the blood vessel from respectives of data of a plurality of sheets of original images collected by scanning a subject injected with a contrast medium by a medical modality, substituting unit configured to substitute pixel values of a plurality of pixels present at a surrounding of the region for a pixel value of the region of the blood vessel in the respectives of the plurality of sheets of images generated by the removing unit, preprocessing unit configured to execute a preprocessing including a noise removing processing for removing noise for data of the plurality of sheets of images subjected to a processing by the substituting unit, and analyzing unit configured to analyze circulation dynamic state information of a substantial portion from the data of the plurality of sheets of images subjected to the preprocessing by the preprocessing unit.

Further, according to the invention, there is provided a program which is a program stored in a memory, read from a computer and described with an executable procedure, said program functionally realizes by executing the program by the computer, blood vessel removing means for removing a data of a region of the blood vessel from a data of an original image collected by scanning a subject injected with a contrast medium by a medical modality; and analyzing means for analyzing circulation dynamic state information of a substantial portion of the subject by applying a preprocessing including a noise removing processing for removing noise to the data of the original image removing the region of the blood vessel by the blood vessel removing means.

Further, according to the invention, there is provided a program which is a program stored in a memory, read by a computer and described with an executable procedure, said computer functionally realizes by executing the program by the computer, blood vessel removing means for removing a data of a region of the blood vessel from respectives of data of a plurality of sheets of original images collected by scanning a subject injected with a contrast medium by a medical modality, substituting means for substituting pixel values of a plurality of pixels present at a surrounding of the region for a pixel value of the region of the blood vessel in the respectives of the plurality of sheets of images generated by the removing means; preprocessing means for executing a preprocessing including a noise removing processing for removing noise to the data of the plurality of sheets of images subjected to a processing by the substituting means; and analyzing means for analyzing circulation dynamic state information of a substantial portion from the data of the plurality of sheets of images subjected to a preprocessing by the preprocessing means.

According to the invention, in the blood stream analysis processing of the brain blood stream analysis or the like, the blood vessel region can firmly be removed from the image in a state in which the partial volume effect hardly remains at the surrounding of the region. Thereby, a measurement with regard to the blood stream analysis by dynamic scanning can be executed highly accurately and high reliably.

DESCRIPTION OF THE PREFERRED EMBODIMENTS

An explanation will be given of preferred embodiments of a medical image processing apparatus and a method of processing a medical image according to the invention.

First Embodiment

A first embodiment will be explained in reference to FIGS. 1 through 8.

Figure 1:
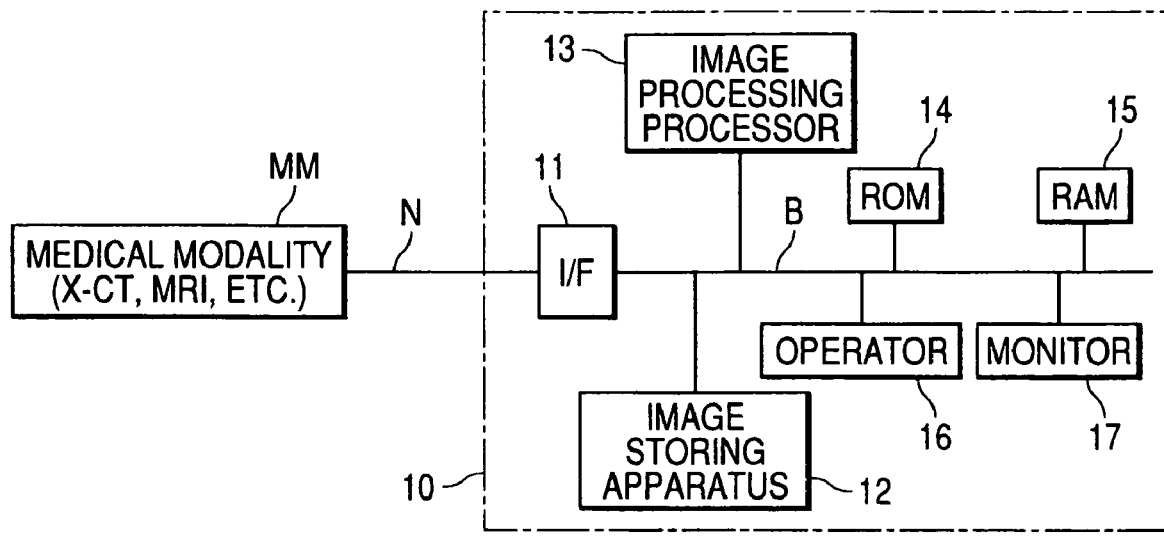
FIG. 1 is a block diagram showing an outline constitution of a medical image processing apparatus according to an embodiment of the invention.

FIG. 1 shows a constitution of a medical image processing apparatus 10 according to the embodiment. As shown by the drawing, the image processing apparatus 10 is connected to a medical modality MM for collecting a two-dimensional or a three-dimensional medical image comprising a digital amount via a network N as communicating means.

The image processing apparatus 10 is an apparatus including a hardware having a function of a computer for providing information and a map image showing a result of analyzing (also measuring) the tissue blood stream of a diagnosed portion of a subject by a software processing based on an installed program.

Specifically, the image processing apparatus 10 is provided with an interface 11 connected to the network N and various units connected to a bus B connected to the interface 11. The units include an image storing apparatus 12, an image processing processor 13, ROM 14, RAM 15, an operator 16 and a monitor 17 for processing to analyze the tissue blood stream.

The image storing apparatus 12 is stored with medical image data of a digital amount collected from a subject (not illustrated) by using the medical modality MM of, for example, an X-ray CT scanner, an ultrasonic diagnosing apparatus, or a magnetic resonance image apparatus. The image processing processor 13 reads an image processing program according to the invention previously stored to ROM 14 to a work memory in starting the program and executes an image processing in accordance with the program.

The image processing corresponds to an image processing executed in a medical image processing apparatus and a method of processing a medical image according to the invention. Although a detailed example will be described later, summarizingly speaking, the image processing relates to a post processing in which from a plurality of sheets of images based on imaging dynamic scanning collected from the same region (same section) of the same portion (for example, the head portion) of a subject by the medical modality MM, a dynamic state of circulation of the portion, further in details, a dynamic state of the tissue blood stream (perfusion) is analyzed (also measured). The image processing is characterized in that a region of the blood vessel of the artery or the vein other than the blood stream (perfusion) passing the capillary of the tissue portion is removed from the image before a processing of analyzing the tissue blood vessel (blood vessel removing processing) and an image of a pixel value comprising only the tissue portion is generated. The image of the tissue portion subjected to the blood vessel removing processing is subjected to an analysis of the tissue blood vessel thereafter.

ROM 14 is previously stored with a program of processing an image as a post processing including the above-described blood vessel removing processing. RAM 15 is used as a temporarily storing memory which is necessary for the image processing and analyzing the tissue blood stream by the image processing processor 13. The operator 16 comprises a keyboard or a mouse and is capable of providing desired information to the image processing apparatus 10 by a surgeon. The monitor 17 is made to display an image or information related to the image processing of analyzing the tissue blood stream including the blood vessel removing processing under a control of the image processing processor 13.

Further, although the image processing apparatus 10 is connected to the medical modality MM as the example via the network N (communicating means), the image processing apparatus 10 may not necessarily be in such a connecting environment but the image processing apparatus 10 may be constituted by a stand alone system. Further, although the image processing apparatus 10 is constituted to execute the image processing as an off-line processing by receiving image data collected by the medical modality MM once, the image processing apparatus 10 is not necessarily limited to such a processing system. For example, a function of the image processing apparatus 10 may integrally be integrated to an image collecting apparatus of the medical modality MM or the like and a collected digital image may be processed almost in real time. Further, the image data collected by the medical modality MM may temporarily be stored to a recording medium of a portable type and the image data may be provided to the image processing apparatus 10 via the recording medium.

Successively, an explanation will be given of a processing of analyzing the tissue blood stream including the blood vessel removing processing centering on the blood vessel removing processing according to the embodiment in reference to FIGS. 2, 3.

According to the example, the medical modality MM is an X-ray CT scanner and image data is collected as follows. Dynamic scanning is executed at a desired section of, for example, the head portion of a subject by the X-ray CT scanner. In the scanning, the subject is rapidly injected with an X-ray contrast medium (for example, iodine contrast medium) which is not provided with the brain blood vessel permeability as a tracer from the vein of, for example, the elbow by using an injector. The contrast medium is made to flow to the brain artery by way of the heart and the lung and flow out to the brain vein from the brain artery by way of the capillary in the brain tissue. Since the contrast medium is not provided with the brain blood vessel permeability, the contrast medium passes the capillary without leaking to outside of the capillary in the normal brain tissue.

As a result, by the dynamic scanning, X-ray transmitting data (live data) reflecting information of behavior of the contrast medium at the desired section of the head portion of the subject is continuously collected at every constant period of time. The collected data is reconstituted by an image reconstituting apparatus of the X-ray CT scanner and is stored at a storing apparatus of the scanner as a dynamic CT image for brain blood stream analysis (CT-perfusion). The dynamic CT image stored at the storing apparatus is transmitted to the image processing apparatus 10 via the communication network N as described above.

Figure 2:
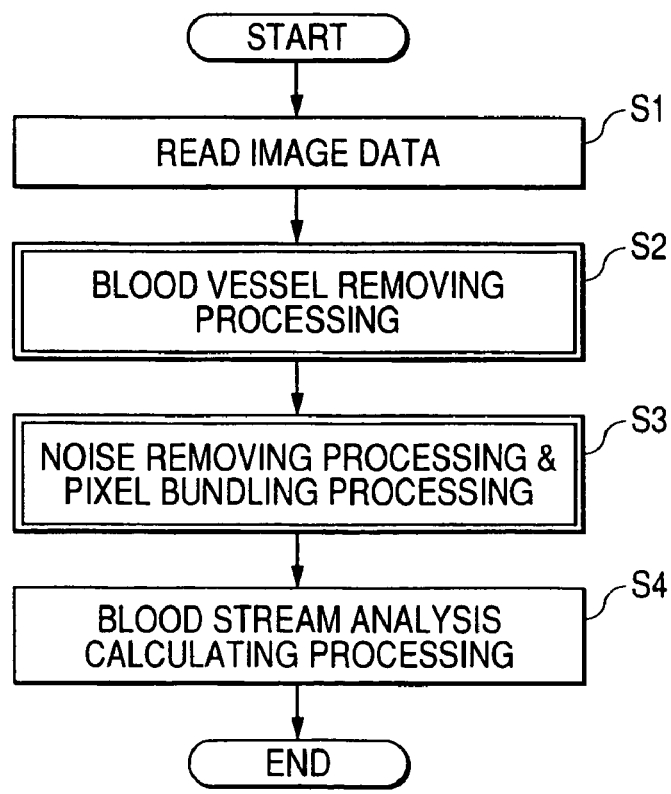
FIG. 2 is a flowchart showing an outline of a processing of analyzing the blood stream of the brain executed in a first embodiment.

At this occasion, the image processing apparatus 10 executes the brain blood stream analysis using the dynamic CT image in line with a procedure an outline of which is shown in FIG. 2.

First, the image processing processor 13 stores a plurality of sheets of the dynamic CT images reconstituted by scanning the same portion of the same subject from the X-ray CT scanner as the medical modality MM via the interface 11 with the image storing apparatus 12 (FIG. 2, step S1).

Successively, the image processing processor 13 executes the blood vessel removing processing for the dynamic CT image stored to the image storing apparatus 12 (step S2). Details of the blood vessel removing processing will be described later.

When the blood vessel removing processing has been finished, the image processing processor 13 executes a noise removing processing and a pixel bundling processing for the image finished with the blood vessel removing processing (step S3), thereafter, executes a processing of analyzing (including a processing of measuring) the brain tissue blood stream (step S4). A result of the analyzing processing is displayed on, for example, the monitor 17 as analyzing information or a map.

Further, the noise removing processing is a processing of smoothing a pixel value by subjecting each image plane to a noise filter, and the pixel bundling processing is a processing of synthesizing a predetermined number of a plurality of pixels into a single pixel for data compression and noise reduction. By the pixel bundling processing, when, for example, an image of a number of pixels of 512×512 is subjected to the pixel bundling processing constituting a single pixel by "2×2" pixels, the image is converted into an image of 256×256 as a whole.

Here, a detailed description will be given of the blood vessel removing processing according to the above-described step S2 in reference to FIG. 3.

Figure 3:
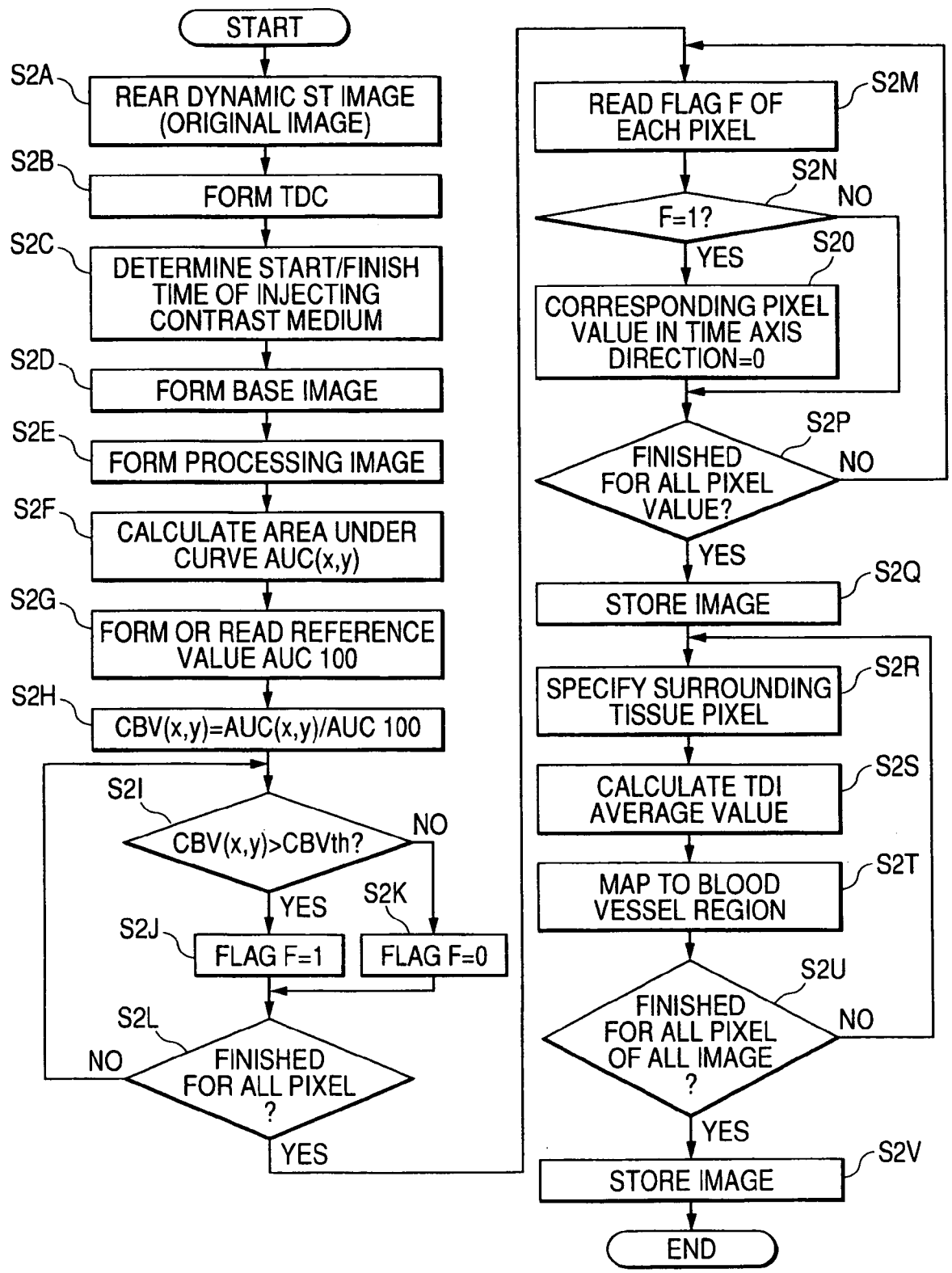
FIG. 3 is a flowchart for explaining a processing of removing the blood vessel executed in the first embodiment.
Figure 4:
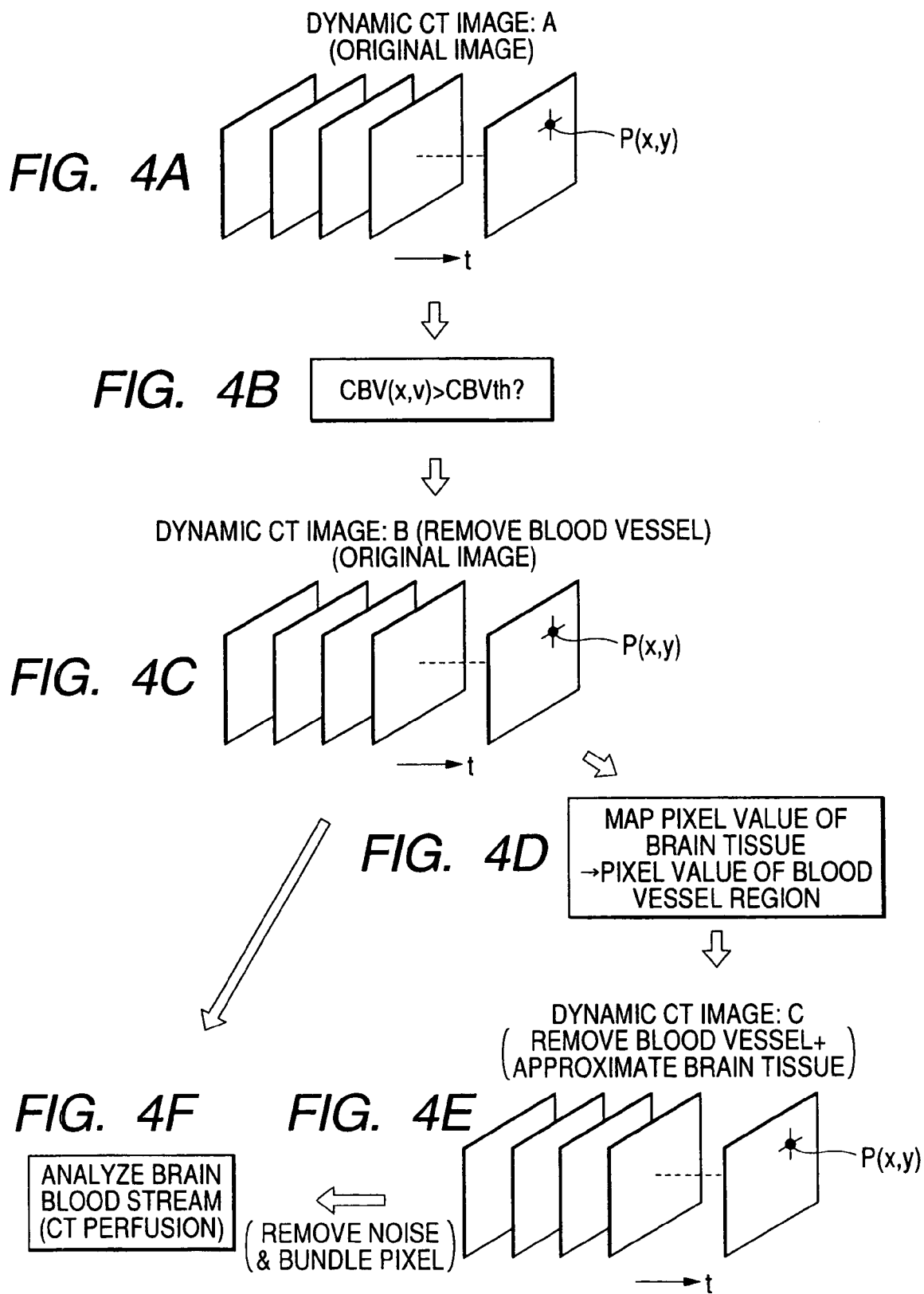
FIG. 4 illustrates views for explaining a procedure of generating a CT image in the blood vessel removing processing.

The image processing processor 13 reads a plurality of sheets of dynamic CT images as original images from the image storing apparatus 12 (FIG. 3, step S2A). Successively, data of a time-density curve (TDC) is formed by time-sequentially reading a pixel value (mean value) for respective image (sectional image) within a designated desired range of ROI with regard to the plurality of sheets of dynamic CT images (step S2B). Further, the image processing processor 13 automatically determines time of starting and time of finishing rapid (bolus) injection of the contrast medium by analyzing a change in the time-density curve (step S2C).

Successively, the image processing processor 13 forms a base image by averaging all of pixel values of CT images taken before rapid injection of the contrast medium for respective pixels (step S2D). At this occasion, a plurality of sheets of processing images, that is, dynamic CT images: A are formed by calculating differences (differences of pixel values) of base images for respective pixels from respectives of the plurality of sheets of CT images after rapid injection of the contrast medium (step S2E: refer to FIG. 4A).

When the step has been finished, the image processing processor 13 calculates TDC of respective pixels by using the plurality of sheets of processing images aligned time-sequentially and calculates a value of an area under curve AUC (x, y) (AUC, x, y: designate positions of respective pixels (refer to FIG. 4A)) (step S2F). Further, the image processing processor 13 reads a value of an area under curve AUC of the superior sagittal sinus (SSS) from a previously stored table or designates a position of the superior sagittal sinus to calculate on the processing image as an example of a previously set a reference value of a blood volume (step S2G). The reference value is designated by AUC 100.

Next, the image processing processor 13 calculates CBV (Cerebral Blood Volume) by executing operation specified below for respective pixels by using the area under curve AUC (x, y) in the respective pixels of the processing images and the reference value AUC 100 (step S2H).

$$CBV(x,y)=AUC(x,y)/AUC\ 100$$

In the calculation, also second pass (secondary circulation) and Hemetocrit are corrected along therewith.

When the step has been finished, the image processing processor 13 proceeds to a threshold processing for respective pixels with regard to CBV. Specifically, when the threshold is designated as CBVth (=AUC 100×desired coefficient), a pixel (x, y) constituting a relationship of the cerebral blood volume CBV (x, y) specified below is recognized not as the blood stream (perfusion) of the capillary in the tissue but as the artery or the vein (blood vessel) to erect a flag F=1 indicating a change in the pixel value P (x, y) of each of the plurality of sheets of dynamic CT images (original image) (steps S2I, S2J).

$$CBV(x,y)>CBVth$$

In contrast thereto, a pixel (x, y) constituting a relationship specified below is recognized as the blood stream (perfusion) of the capillary in the brain tissue to erect a flag F=0 indicating that the pixel values P (x, y) of the plurality of sheets of dynamic CT images (original image) are not changed (steps S2I, S2K).

$$CBV(x,y)\leq CBVth$$

The threshold processing is executed for all of the pixels (x, y) of the plurality of dynamic CT images (step S2L).

When it has been finished to determine whether the pixel is the artery or the vein (blood vessel) or the blood stream of the capillary in the tissue in this way, the image processing processor 13 executes processings of changing the pixel values of the pixels (x, y) determined as the artery or the vein (blood vessel) for the respective pixels (x, y) of the plurality of sheets of dynamic CT images (original images) (steps S2M through S2P).

That is, the pixel (x, y) is designated from all of the pixels (x, y) constituting the object of the threshold processing, the flag F is read and it is determined whether the flag F=1 (pixel value change) (steps S2M, S2N). When F=1 (YES) in the determination, P (x, y)=0 is set to the pixel values P (x, y) of all the pixels in a time axis direction of the plurality of sheets of dynamic CT images common to the pixels (x, y) (that is, all the pixels of the plurality of sheets of dynamic images positionally in correspondence with each other) (step S2O). Thereby, the pixel values P (x, y) of all the pixels in the time axis direction of the pixels (x, y) determined as the artery or the vein are forcibly changed to P (x, y)=0.

On the contrary, in the case of F=0 (NO), the pixel value change processings are skipped. Therefore, when the pixel (x, y) is determined not to be the artery or the vein but to be the blood stream in the brain tissue, all of the pixel values in the time axis direction in correspondence with the pixel (x, y) are not changed but the original pixel values are maintained. The processing of changing the pixel values is executed for all the pixels by determining the flag (step S2P).

As a result, as shown by FIGS. 4A through 4C, the blood vessel (the artery or the vein) is removed by the threshold processing of the cerebral blood volume CBV (x, y) based on the area under curve AUC of the time-density curve (TDI) from the plurality of sheets of dynamic CT images: A taken by the X-ray CT scanner. As a result, a plurality of sheets of dynamic CT images: B subjected to the blood vessel removing processing are generated.

When the processing of changing the pixel value of the blood vessel (the artery or the vein) has been finished, the image processing processor 13 stores the plurality of sheets of dynamic CT images: B removed of the blood vessel region in the image storing apparatus 12 (step S2Q).

Successively, the image processing processor 13 executes a processing of substituting pixel values of the brain substantial portion for the pixel region determined as the blood vessel with regard to the plurality of sheets of dynamic CT images: B (steps S2R through S2U).

Specifically, pixels present at a surrounding of the pixel region determined as the blood vessel (pixels of the brain substantial portion) are specified (step S2R). According thereto, for example, there are designated a predetermined number of pixels from respective points on a boundary of the blood vessel region to outer sides along orthogonal directions. Successively, time-density curves of the specified outer side pixel regions are calculated for the respective pixels and mean values thereof are calculated (step S2S) The pixel values of the blood vessel region are substituted for by the mean values (step S2T). A series of substituting processings are executed for all of the plurality of sheets of dynamic CT images (step S2U).

Thereby, the pixel values of the blood vessel region are substituted for by the mean values of the pixel values of the brain tissue at a surrounding to map and therefore, the region inherent to the blood vessel disappears from the image or is expressed to narrow. That is, the blood vessel region is constituted by the pixel values approximated to those of the brain tissue. As a result, a plurality of sheets of dynamic CT images: C subjected to the processing of substituting for the pixel values of the blood vessel region is formed (refer to FIGS. 4C through 4E), and the CT images: C are stored to the image storing apparatus 12 (step S2V).

The dynamic CT image: B subjected to the above-described blood vessel removing processing, or the dynamic CT image: C subjected to the blood vessel removing processing and the tissue approximating processing is used for analyzing the brain blood stream and a circulation dynamic image is generated (refer to FIG. 4F). The brain blood stream analysis is executed by the image processing processor 13.

Figure 5:
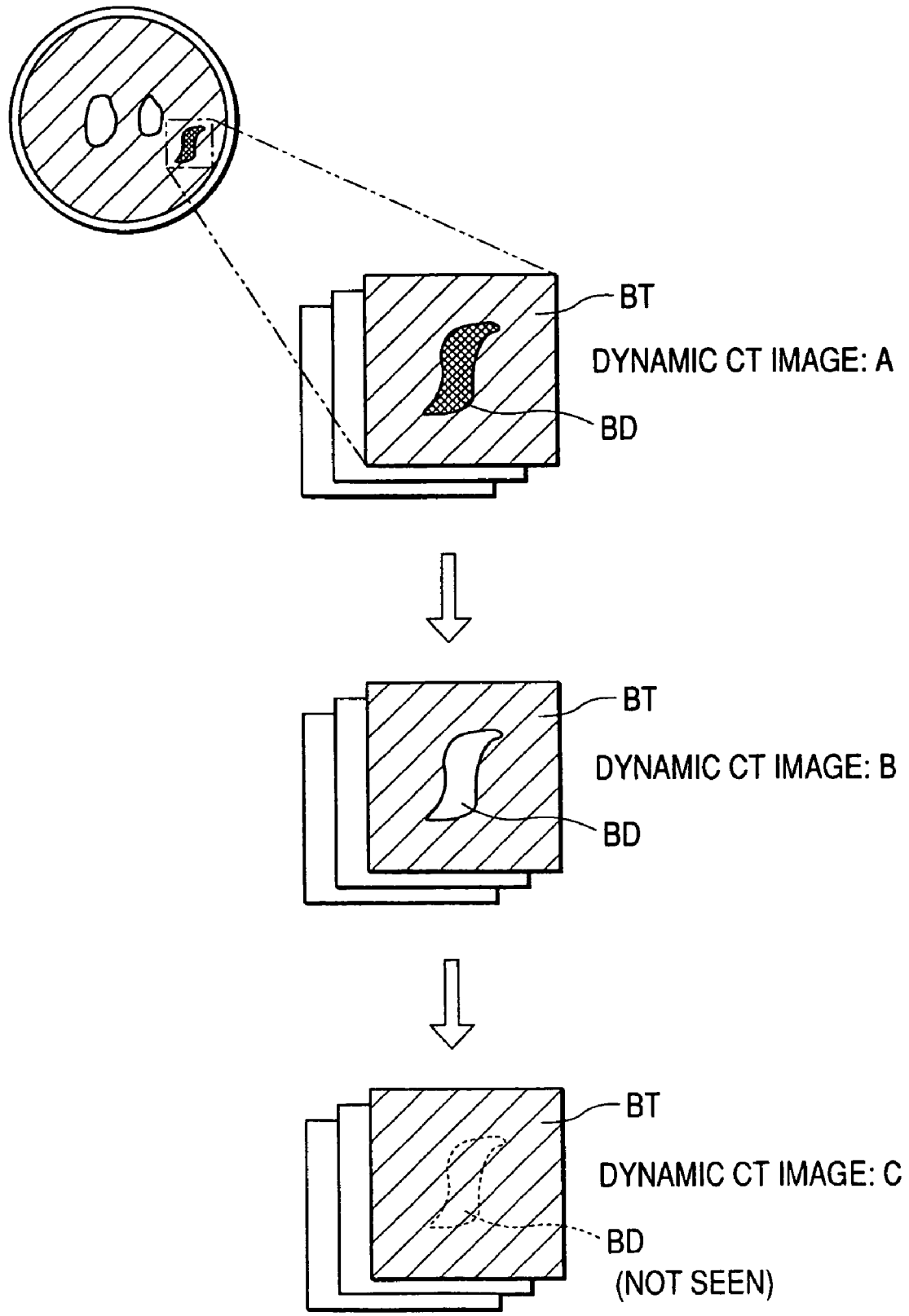
FIG. 5 is a view for schematically explaining the CT image generated in the blood vessel removing processing.

FIG. 5 shows the three kinds of dynamic CT images: A, B, C generated by the series of processings shown in FIGS. 2 through 4 to facilitate to understand. In FIG. 5, a region BD indicates the brain tissue, a region BD indicates the blood vessel (the artery or the vein). A portion of a vicinity of the blood vessel BD of the brain tissue BT appearing in the dynamic CT image: A undergoes the partial volume effect of the blood vessel BD. The dynamic CT image: A is converted into the dynamic CT image: B by being subjected to the threshold processing based on the area under curve as described above. At this occasion, also the blood vessel region is simultaneously recognized (FIG. 3, steps S2K, S2M through S2P). The pixel value of the blood vessel region BD of the dynamic CT image: B becomes vacant by pixel value=0. The dynamic CT image: B is converted into the dynamic CT image: C by the approximating processing of mapping the blood vessel region by the pixel values of the brain tissue. Thereby, almost all of the CT images are filled by the brain tissue and the original blood vessel region BD is also approximated by the pixel values of the brain tissue. Therefore, in the dynamic CT image: C, the blood vessel region BD hardly appears.

Next, an explanation will be given of a selective display processing executed by the image processing processor 13 in reference to FIG. 6.

The image processing processor 13 can switch a kind of a display image of a circulation dynamic state image (CBF, CBV, MTT) in the midst of the processing of analyzing (including the processing of measuring) the tissue blood stream executed at the above-described step S4 of FIG. 2, in comparing a quantitative value of the analysis map after the analyzing processing, or in optical diagnosis.

Figure 6:
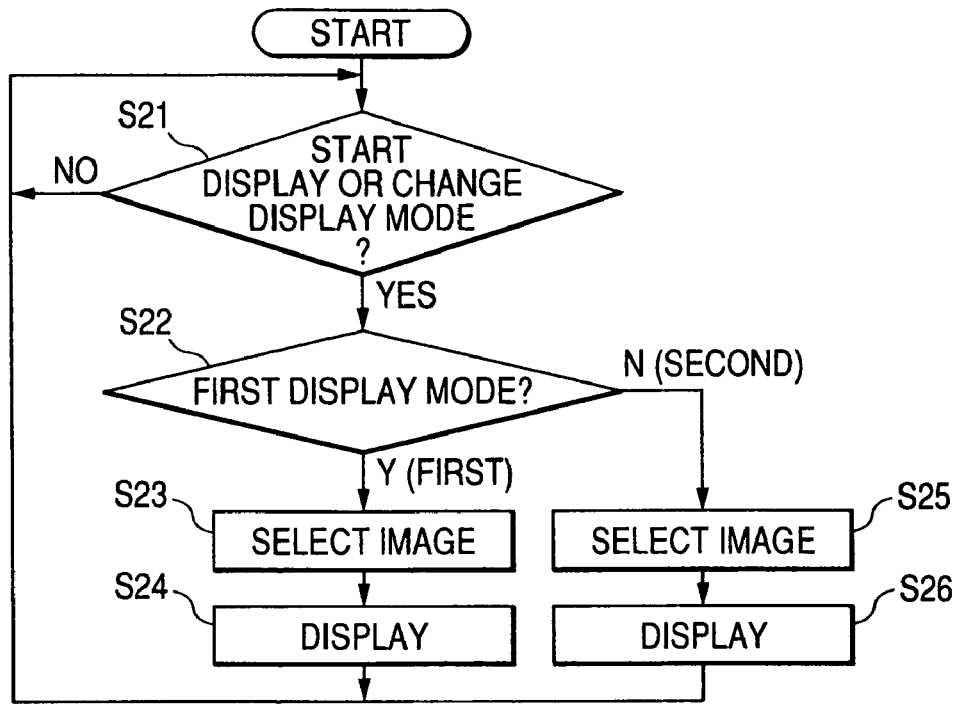
FIG. 6 is an outline flowchart showing a processing of selecting a display mode.

That is, as shown by FIG. 6 a surgeon instructs a display from the operator 16 and determines whether a display mode is a first display mode (a mode displaying the circulation dynamic state image: B removing the blood vessel region), or a second display mode (a mode displaying the circulation dynamic state image: C removing the blood vessel region and substituting the value of the brain tissue at the surrounding for the circulation dynamic state (steps S21, S22). As a result, the dynamic images to be displayed are selected for respectives of the first display mode and the second display mode to display on the monitor 17 (steps S23 through S26). Thereby, the surgeon can switch to display the images of the two modes as necessary to be used for reading the image.

As described above, in the case of the brain blood stream analysis (CT-perfusion) according to the embodiment, first, the blood vessel region is removed from the plurality of dynamic CT images (original image) taken by the dynamic scanning and thereafter, the noise removing processing and the pixel bundling processing are executed. An order of reaching "noise removing processing and the pixel bundling processing" from "removing the blood vessel region" differs from that of the related art.

Figure 7:
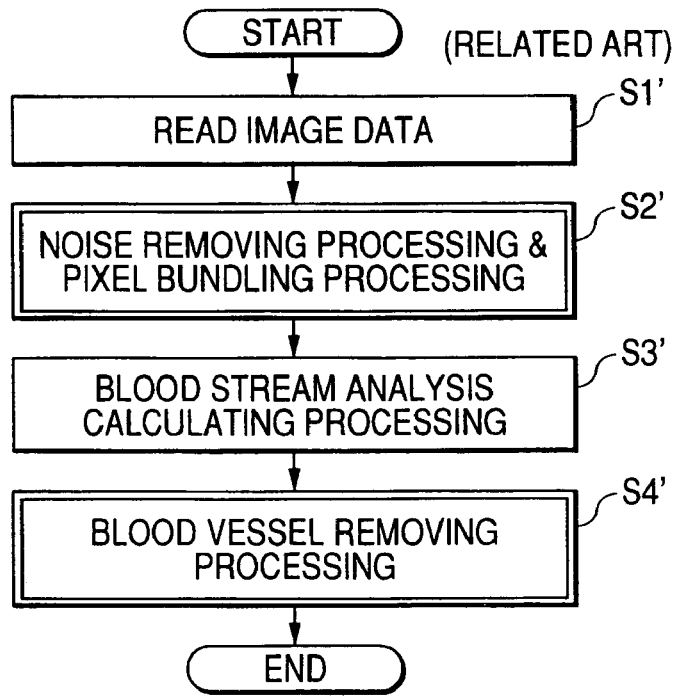
FIG. 7 is a flowchart showing an outline of a processing of analyzing the blood stream of the brain of a related art illustrated for explaining a comparison with the invention.

According to an order of processings of the related art, as shown by FIG. 7, the processings are successively executed such that data of the plurality of dynamic CT images (original images) are read (step S1'), the noise removing processing and the pixel bundling processing for the original images are executed (step S2'), the blood stream analysis calculating processing is executed (step S3'), and a processing of removing the blood vessel region from various maps of the analysis result is executed (step S4').

Therefore, in the case of the order of processings of the related art, by the noise removing processing and the pixel bundling processing executed at step S2', owing to the partial volume effect of the blood vessel (the artery or the vein), an influence of a high pixel value of the blood vessel is widened to the surrounding of the blood vessel, that is, to the region of the brain tissue. That is, since the noise removing processing and the pixel bundling processing constitute the object of the processing always by the plurality of pixels at a vicinity, in processing the region brought into contact with the contour of the blood vessel of the brain tissue, the high pixel value of the blood vessel region pushes up the pixel value of the brain tissue and the pixel value of the brain tissue becomes higher than an original value of the pixel value per se.

Figure 8A:
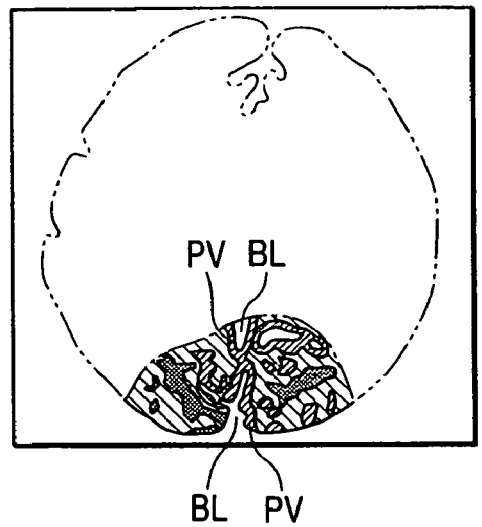
FIG. 8A through 8C manually copy portions of images which are actually provided, showing an analysis map provided by analyzing the brain blood stream according to the related art, an analysis map provided by analyzing the brain blood stream subjected to the blood stream removing processing, and an analysis map provided by analyzing the brain blood stream subjected to the blood stream removing processing and a tissue approximating processing.
Figure 8B:
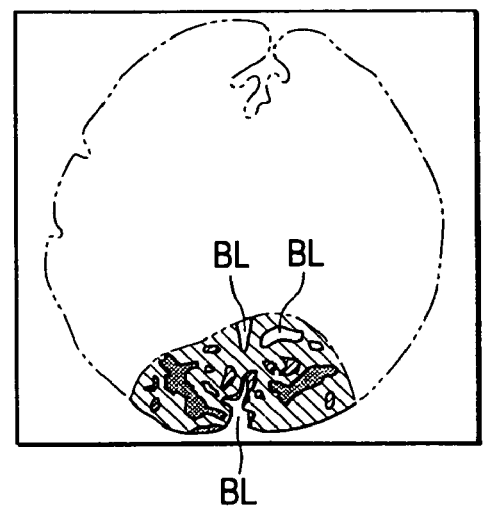

Although a degree of widening the high pixel value region owing to the partial volume effect is changed by a degree of the pixel value provided to the blood vessel (the artery or the vein) and a size of the region of the blood vessel, as schematically shown in FIG. 8A, generally, the region is widened over a total of the surrounding of the blood vessel (the artery or the vein).

FIG. 8A is a map after analyzing the brain blood stream according to the related art and is a partial schematic view of a map removing the blood stream region BL. A hatching of the region PV rising to the right slenderly presents along the surrounding of the blood vessel region BL indicates a region influenced by the partial volume effect of the blood vessel. Although the region PV is actually a portion of the brain tissue, the region PV is displayed as a kind of artifact such that as if the blood stream by the artery or the vein were present. When the region PV influenced by the partial volume effect remains, not only the image becomes difficult to read to deteriorate an image reading efficiency but also the blood stream value of the substantial portion of the brain rises more than the original value, which can also constitute an error in measurement.

Figure 8C:
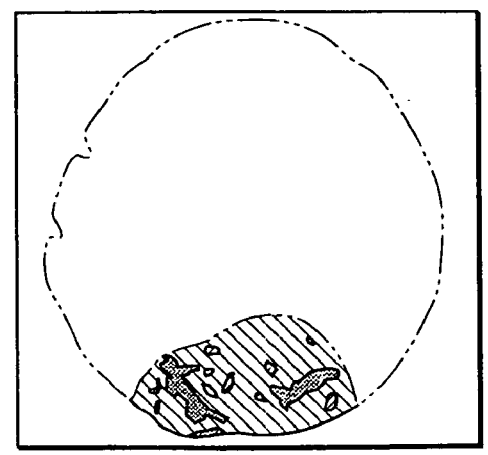

In contrast thereto, in the case of the embodiment, as described above, the blood vessel (the artery or the vein) region is removed from the original image and thereafter, the noise removing processing and the pixel bundling processing are executed. Therefore, first, only the brain tissue constituting the object of analyzing the brain blood stream can be extracted (refer to FIG. 8B). In addition thereto, at a stage of executing the noise removing processing and the pixel bundling processing, the blood vessel region, that is, the region in which the pixel value is normally higher than that of the brain tissue has already been removed firmly. Further, a large number of the pixels of the region which have been inherently those of the blood vessel are substituted for by the approximated value of the value of the brain tissue at the surrounding. Therefore, even when the noise removing processing and the pixel bundling processing are executed, the partial volume effect of the blood vessel (the artery or the vein) is almost nullified and the blood stream value at the surrounding of the removed blood vessel becomes hardly high or is considerably reduced. As shown by FIG. 8C, the pixel value of the blood vessel (the artery or the vein) of the analysis map provides an image substituted for by the approximated value of the tissue of the surrounding.

Therefore, it is resolved that the efficiency of the image reading operation is influenced by remaining of the partial volume effect. Further, as shown by FIG. 8C, the image substituting for the blood vessel region by the pixel value of the brain tissue at the surrounding looks like an image taken by nuclear medical diagnosing apparatus (SPECT, PET) in an outlook thereof and therefore, the image is easy to see by a reader. Further, since there is not the influence of the partial volume effect of the blood vessel (the artery or the vein), the blood stream value of the substantial portion of the brain can highly accurately be measured. Therefore, the blood stream of the substantial portion of the brain can further accurately and further reliably be evaluated in analyzing the brain blood stream.

Further, according to the embodiment, the first display mode (the mode of displaying the plurality of sheets of dynamic images: B removing the blood vessel region) or the second display mode (the mode of displaying the circulation dynamic state image: C substituting for the pixel value of the blood vessel region by the value of the brain tissue) can selectively be switched by instructing the display by the surgeon from the operator 16.

Thereby, in comparing the quantitative value of the analysis maps, the first display mode (refer to FIG. 8B) simply removing the blood vessel region can be selected and in optically observing the image, the image of the second display mode (refer to FIG. 8C) which is the image used to be seen and looks like an SPECT image or a PET image in an outlook thereof and in which the blood vessel region is filled by the approximated value of TDC of the brain tissue at the surrounding can be selected. The function of capable of switching to select the images is convenient in reading the image.

Second Embodiment

An explanation will be given of an image processing apparatus and a method of processing a medical image of a second embodiment according to the invention in reference to FIGS. 9, 10A and 10B. Further, in the second embodiment, constituent elements equivalent to or the same as those of the first embodiment are attached with the same notations and an explanation thereof will be omitted or simplified.

The image processing apparatus according to the second embodiment relates to a modified example of the first embodiment and is particularly characterized in that also the image of the blood vessel can be displayed. Therefore, the blood vessel removing processing, the noise removing processing & pixel bundling processing, and the blood stream analysis processing which have been explained centering on FIGS. 2 through 5 in the first embodiment are similarly executed also in the second embodiment.

As described above, in forming the dynamic CT image: B, by flag F=1, the blood vessel region in the respective dynamic CT images: A is recognized. The blood vessel region is a region designated by, for example, the reference notation BD in FIG. 5.

Figure 9:
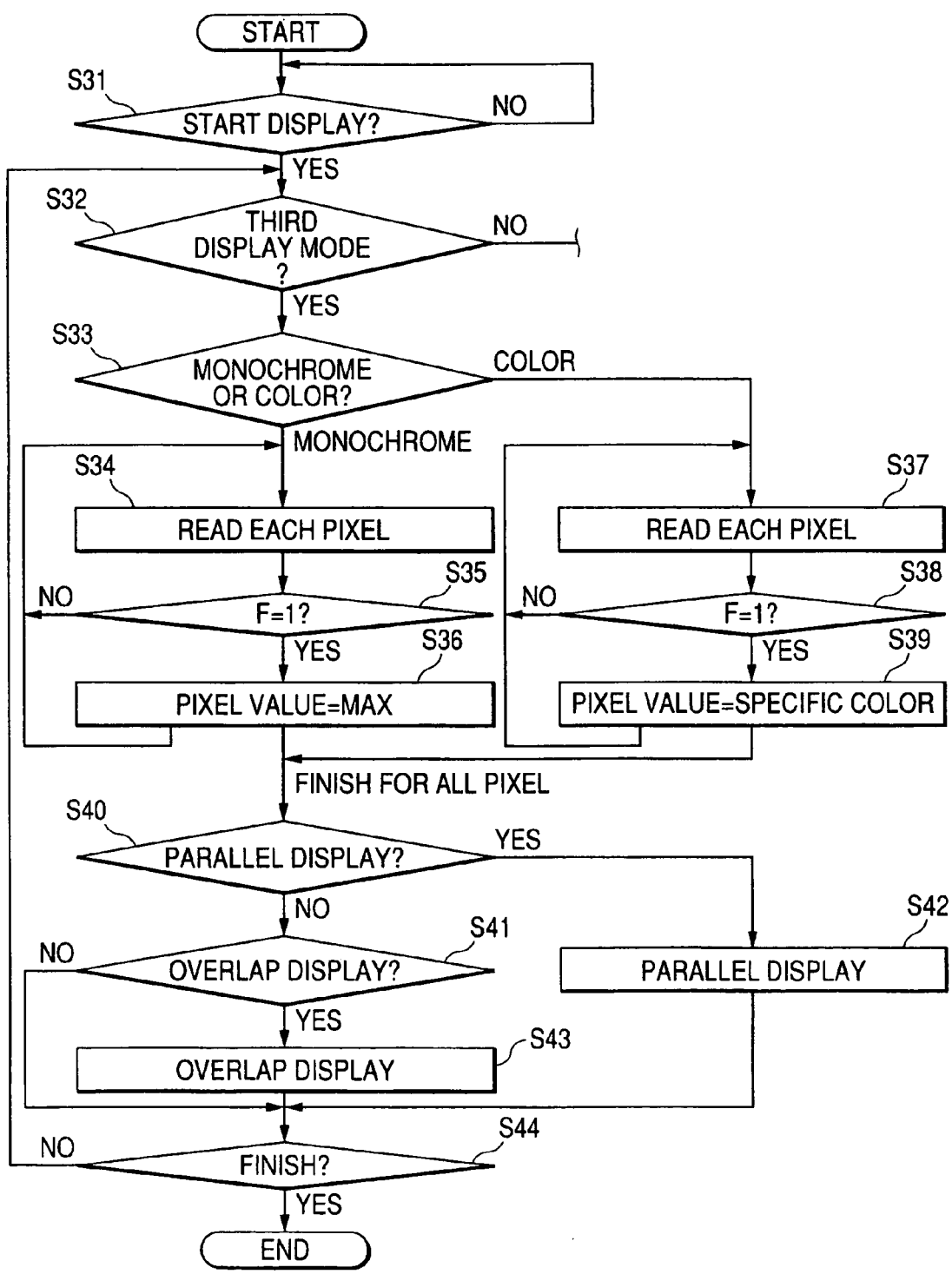
FIG. 9 is a flowchart for explaining an outline of a display processing accompanied by a display of a blood vessel image executed by a second embodiment.

Therefore, the image processing processor 13 executes a processing for displaying the blood vessel image using flag F=1 as shown by FIG. 9.

First, the image processing processor 13 determines whether the image is started to display based on the instruction of the surgeon from the operator 16 (step S31), and determines whether the display mode is a third display mode when started (step S32). The third display mode is a mode of displaying an image of analyzing perfusion of the brain tissue accompanied by the image of the blood vessel (the artery or the vein).

Further, the third display mode may be constituted by a mode of displaying an image before analyzing perfusion, that is, any image of the dynamic CT image: C removing the blood stream and approximating the blood vessel by the brain tissue as it is accompanied by the blood vessel image.

In the case of executing a display by the third display mode, the image processing processor 13 determines whether the blood vessel image is displayed by monochrome or displayed by color based on the instruction of the surgeon from the operator 16 (step S33).

When the determination indicates a monochrome display, the image processing processor 13 successively reads respective pixels of respective images from the image storing apparatus 12 and determines whether flag F=1 is erected at the pixels (steps S34, S35). Thereby, a pixel value a maximum value is set for the pixel in which flag F=1 is determined (step S36). Normally, when the pixel value of each pixel is indicated by 12 bits, a pixel value of a perfusion image or an image of analyzing the perfusion image is about 200 through 1000 and therefore, for example, the maximum value=2048 is instructed for the pixel value.

On the other hand, when the surgeon instructs that the blood vessel image is displayed by color (step S33), similarly, respective pixels of respective images are successively read, and when flag F=1 is erected for the pixels, pixel=specific color is designated (steps S37 through S39). As a color, a specific color which is not used in normal perfusion is preferable and the color is, for example, gray color.

When the setting has been finished, the image processing processor 13 determines whether the image of analyzing perfusion and the blood vessel image are displayed parallely or the blood vessel image is displayed overlappingly on the image of analyzing perfusion interactively with the surgeon (steps S40, 41). In accordance with the determination, the image processing processor 13 executes the parallel display or the overlap display (steps S42, S43). The display processing can be repeated as necessary (step S44).

Figure 10A:
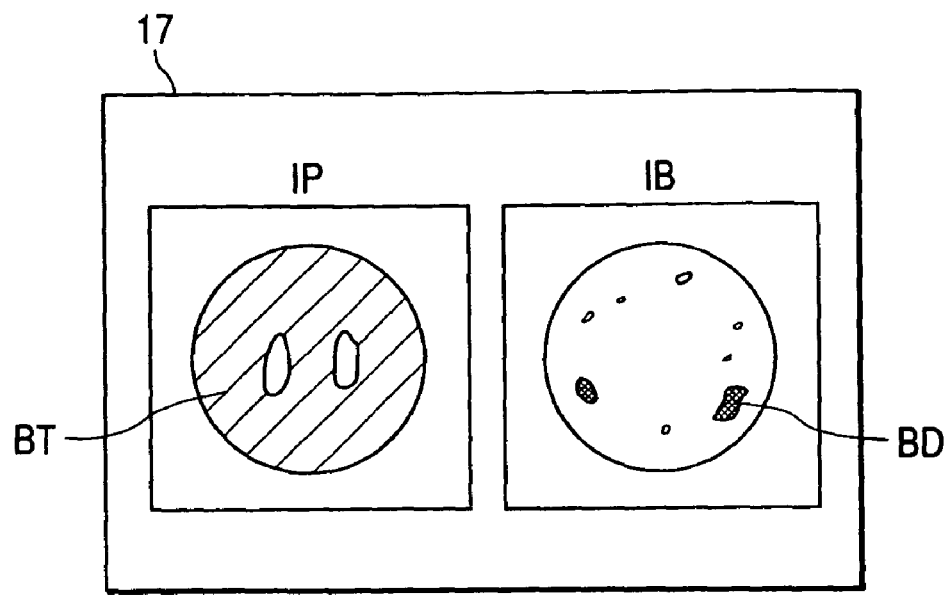
FIGS. 10A and 10B are schematic views showing a parallel display and an overlap display of a perfusion image and a blood vessel image.

Therefore, when the parallel display is designated, as shown by FIG. 10A, a perfusion image IP of the brain tissue and a blood vessel image IB of a section common to the plurality of sheets of dynamic CT images are displayed in parallel on, for example, the same screen of the monitor 17. In this case, the blood vessel region BD is illustrated by a maximum brightness or a specific color of gray color or the like in the blood vessel image IB and therefore, a position and a range of the blood vessel is easy to see. Therefore, a comparison can be carried out while comparing a positional relationship with a low blood volume region of the contiguous perfusion image IP.

Figure 10B:
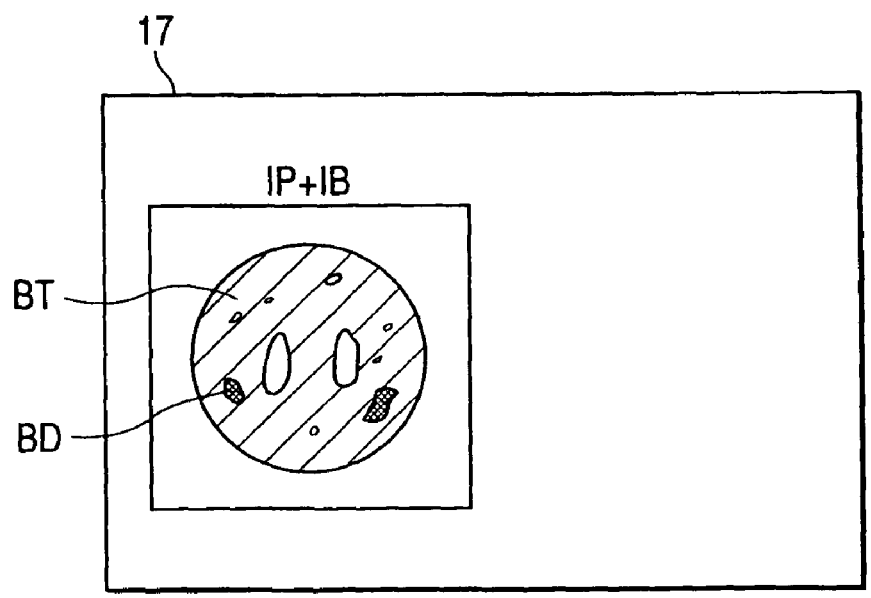

On the other hand, when the overlap display is designated, as shown by FIG. 10B, the blood vessel image IB is displayed overlappingly on the perfusion image IP of the brain tissue on the screen of the monitor 17. In this case, the blood vessel region BD is illustrated by the maximum brightness or the specific color of gray color or the like in the blood vessel image IB and therefore, the position and the range of the blood vessel can be seen at a glance also on the perfusion. Therefore, the respective low blood volume regions of the perfusion image IP can be read by recognizing the positional relationship with the blood vessel.

In this way, according to the embodiment, in addition to the function explained in the first embodiment, abundant formation of the display mode is achieved to achieve operation and effect of considerably assisting the diagnosis.

Further, the invention is not limited to the above-described constitutions of the embodiments but can pertinently be modified within the range not deviated from a gist thereof described in the scope of claims.

For example, although in the processing of step S3 of FIG. 2, the image processing processor 13 executes both of the noise removing processing and the pixel bundling processing, the image processing processor 13 may execute only either one thereof.

Further, in the processings of FIG. 3, the image processing processor 13 may permit only the above-described first display mode by executing only up to the processing at step S2Q. That is, in this case, although the removed blood vessel region is not filled by the approximated value of TDC of the brain tissue at the surrounding, a further accurate brain blood stream analysis can be executed by firmly excluding the above-described influence of the partial volume effect owing to the blood vessel (the artery or the vein).

Further, when executing the processing of removing the blood vessel region related to step S2 of the processing procedure of the brain blood stream analysis, the noise removing processing can also be executed prior to the processing of removing the blood vessel region so far as the noise removing processing is a noise removing processing by which the partial volume of the blood vessel is prevented from being widened.

Further, the medical image processing apparatus and the method of processing the medical image according to the invention are not limited to those constituting the object by the tissue blood stream (brain blood stream) as described above but may be embodied for analyzing the blood stream, for example, the blood stream of the tissue of the liver, the heart or the like other than the brain. Further, also the medical modality for collecting the original image is not limited to the X-ray CT scanner but may be an ultrasonic apparatus, a magnetic resonance imaging apparatus or the like.

What is claimed is:

1. A medical image processing apparatus comprising:
a blood vessel removing unit configured to remove a data of a region of a blood vessel from respectives of data of a plurality of sheets of original images collected by scanning a subject injected with a contrast medium by a medical modality;
a substituting unit configured to substitute values of pixels inside the region of the blood vessel with values of pixels present at a surrounding of the region of the blood vessel in respectives of a plurality of sheets of images generated by the blood vessel removing unit;
a preprocessing unit configured to execute a preprocessing including a noise removing processing for removing noise for data of a plurality of sheets of images subjected to a processing by the substituting unit; and
an analyzing unit, including a processor, configured to analyze circulation dynamic state information of a substantial portion of the subject from data of a plurality of sheets of images subjected to the preprocessing by the preprocessing unit.

2. The medical image processing apparatus according to claim 1, wherein the preprocessing includes a pixel bundling processing for bundling a plurality of predetermined pixels to a single pixel in addition to the noise removing processing.

3. The medical image processing apparatus according to claim 1, wherein the contrast medium is a contrast medium which is not permeable through the blood vessel.

4. The medical image processing apparatus according to claim 1, wherein the scanning is dynamic scanning of collecting the data of the plurality of sheets of original images.

5. The medical image processing apparatus according to claim 4, wherein the circulation dynamic state information is perfusion.

6. The medical image processing apparatus according to claim 5, wherein the blood vessel removing unit comprises:
a curve forming unit configured to form data of time-density curves (TDC) from the data of the plurality of sheets of original images of respective pixels;
a calculating unit configured to calculate values of areas under the curves of the curves of the respective pixels with regard to the curve data formed by the time-density curve forming unit;
a determining unit configured to determine whether the values of the areas under the curves of the respective pixels calculated by the calculating unit are larger than a predetermined threshold;
a recognizing unit configured to recognize that portions of the pixels having the values of the areas under the curves larger than the threshold determined by the determining unit fall in the region of the blood vessel; and
a removing unit configured to remove the region of the blood vessel recognized by the recognizing unit from the respectives of the data of the plurality of sheets of the original images.

7. The medical image processing apparatus according to claim 6, wherein the substituting unit is a unit for substituting a mean value of a plurality of pixel values present at a surrounding of the region for the pixel values of the region of the blood vessel of the respectives of the plurality of sheets of images formed by the removing unit.

8. The medical image processing apparatus according to claim 7, further comprising:
an image display unit configured to selectively display the image generated by the removing unit and the image generated by the substituting unit.

9. The medical image processing apparatus according to claim 7, further comprising:
an image display unit configured to display both of the image analyzed by the analyzing unit and the image indicating the region of the blood vessel recognized by the recognizing unit.

10. The medical image processing apparatus according to claim 9, wherein the image display unit is a unit configured to display the image analyzed by the analyzing unit and the image indicating the region of the blood vessel recognized by the recognizing unit in parallel so that the image analyzed by the analyzing unit and the image indicating the region of the blood vessel recognized by the recognizing apparatus do not overlap each other.

11. The medical image processing apparatus according to claim 9, wherein the recognizing unit includes unit configured to set a pixel value of a highest value to the pixel indicating the region of the blood vessel or pixel information indicating a specific color to the pixel; and
wherein the image display unit is a unit for displaying the image indicating the region of the blood vessel recognized by the recognizing unit overlappingly on the image analyzed by the analyzing unit.

12. The medical image processing apparatus according to claim 1, wherein the medical modality is an X-ray CT apparatus and the original image is an X-ray CT image.

13. An image processing apparatus comprising:
a curve forming unit configured to form data of time-density curves (TDC) of respectives of data of a plurality of sheets of original images for respective pixels;
a calculating unit, including a processor, configured to calculate values of areas under curves of the curves of the respective pixels with regard to curve data formed by the time-density curve forming unit;
a comparing unit configured to compare the values of the areas under curves calculated by the calculating unit with a predetermined threshold; and
a recognizing unit configured to recognize that portions of the pixels having the values of the areas under the curves exceeding the threshold by the comparing unit fall in the region of the blood vessel.

14. The image processing apparatus according to claim 13, further comprising:
a removing unit configured to remove the region of the vessel recognized by the recognizing unit from the respectives of the plurality of sheets of original images.

15. A method of processing a medical image comprising:
removing a data of a region of a blood vessel from respectives of data of a plurality of sheets of original images collected by scanning a subject injected with a contrast medium by a medical modality;
substituting values of pixels inside the region of the blood vessel with values of pixels present at a surrounding of the blood vessel in respectives of a generated plurality of sheets of images;
executing a preprocessing including a noise removing processing for removing noise for data of a plurality of sheets of images subjected to the above-described removing and substituting processings; and
analyzing, by a processor, circulation dynamic state information of a substantial portion from data of a plurality of sheets of images subjected to the preprocessing.

16. An image processing apparatus comprising:
a storing apparatus configured to store data of a plurality of sheets of original images collected by scanning a subject injected with a contrast medium by a medical modality; and
a processor configured to execute respective processings of removing a data of a region of a blood vessel from respectives of the data of the plurality of sheets of original images stored to the storing apparatus, substituting values of pixels inside the region of the blood vessel with values of pixels present at a surrounding of the region of the blood vessel in respectives of a generated plurality of sheets of images, executing a preprocessing including a noise removing processing for removing noise for data of a plurality of sheets of images subjected to the above-described processings, and analyzing circulation dynamic state information of a substantial portion from data of a plurality of sheets of images subjected to the preprocessing.

17. A non-transitory computer readable medium including computer executable instructions which when executed by a computer cause the computer to comprise:
blood vessel removing means for removing a data of a region of a blood vessel from respectives of data of a plurality of sheets of original images collected by scanning a subject injected with a contrast medium by a medical modality;
substituting means for substituting of pixels inside the region of the blood vessel with values of pixels present at a surrounding of the region of the blood vessel in respectives of a plurality of sheets of images generated by the removing means;
preprocessing means for executing a preprocessing including a noise removing processing for removing noise for data of a plurality of sheets of images subjected to a processing by the substituting means; and
analyzing means for analyzing circulation dynamic state information of a substantial portion from data of a plurality of sheets of images subjected to the preprocessing by the preprocessing means.

* * * * *